United States Patent
Acuna et al.

(10) Patent No.: US 6,805,893 B2
(45) Date of Patent: Oct. 19, 2004

(54) MERCAPTO-ALKANOL FLAVOR COMPOUNDS

(75) Inventors: Gonzalo Acuna, Dietikon (CH);
Markus Gautschi, Am Stutz (CH);
Frank Kumli, Niedererlinsbach (CH);
Joachim Schmid, Volketswil (CH);
Janos Zsindely, Leisibûel (CH)

(73) Assignee: Givaudan SA, Vernier (CH)

( * ) Notice: Subject to any disclaimer, the term of this patent is extended or adjusted under 35 U.S.C. 154(b) by 0 days.

(21) Appl. No.: 10/459,251

(22) Filed: Jun. 11, 2003

(65) Prior Publication Data

US 2004/0047960 A1 Mar. 11, 2004

Related U.S. Application Data

(63) Continuation-in-part of application No. 09/579,633, filed on May 26, 2000, now Pat. No. 6,610,346.

(30) Foreign Application Priority Data

May 28, 1999 (EP) .............................................. 9910416

(51) Int. Cl.[7] ................................................ A23L 1/22
(52) U.S. Cl. ...................... 426/535; 426/534; 426/590; 426/650
(58) Field of Search ................................ 426/534, 535, 426/590, 650

(56) References Cited

U.S. PATENT DOCUMENTS

| | | | |
|---|---|---|---|
| 3,892,878 A | 7/1975 | Wilson et al. | 426/534 |
| 3,970,689 A | 7/1976 | Stoffelsma et al. | 260/488 |
| 4,053,656 A | 10/1977 | Stoffelsma et al. | 426/535 |
| 6,231,912 B1 | 5/2001 | Widder et al. | 426/535 |

FOREIGN PATENT DOCUMENTS

| | | | |
|---|---|---|---|
| DE | 2316456 | 4/1973 | |
| EP | 924198 | 6/1999 | ......... C07C/323/12 |
| GB | 1429314 | 4/1976 | ........... A23L/1/226 |

OTHER PUBLICATIONS

Bouchilloux et al., *Identification of Volatile and Powerful Odorous Thiols in Bordeaux Red Wine Varieties*, J. Agric. Food Chem. 1998, 46, 3095.
Engel et al., *Identification of New Sulfur–Containing Volatiles in Yelloow Passion Fruits (Passiflora edulis f. flavicarpa)*, J. Agric. Food Chem. 1991, 39, 2249.
Holscher et al., *Prenyl Alcohol—Source for Odorants in Roasted Coffee*, J. Agric Food Chem 1998, 46, 3095.
Olsen et al., *Onion–like off–flavor in beer: Isolation and identification of the culprits*, Carlsberg Res. Commun. (1968) 53(1) (Abstract) Stn Caplus XP 002120546.
Tominaga et al., *Identification of New Volatile Thiols in the Aroma of Vitis Vinifera L. Var. Sauvignon Blanc Wines*, Flavour Fragrance J. 1998, 13, 159.
Werkhoff et al., *Vacuum Headspace Method in Aroma Research: Flavor Chemistry of Yelow Passion Fruits*, Flavour Fragrance J. 1998, 13, 159.

Primary Examiner—Leslie Wong
(74) Attorney, Agent, or Firm—Wood, Herron & Evans, L.L.P.

(57) ABSTRACT

New diastereoisomer-enriched 3-mercapto-alkanols are disclosed. The compounds, namely 3-mercapto-2-methyl-butan-1-ol and/or 3-mercapto-3-methyl-hexan-1-ol, and the stereoisomers of each, are used to flavor products, such as foods and/or beverages. Methods for the preparation of both diastereoisomers of 3-mercapto-2-methyl-butan-1-ol are also disclosed.

47 Claims, No Drawings

MERCAPTO-ALKANOL FLAVOR COMPOUNDS

This application is a Continuation-In-Part of the U.S. patent application Ser. No. 09/579,633 filed May 26, 2000, now U.S. Pat. No. 6,610,346, which claims priority to European Patent Application Serial No. 99110416.7 filed May 28, 1999.

FIELD OF THE INVENTION

The present invention relates to new 3-mercapto-alkanols enriched in particular stereoisomers, to flavoring compositions containing and to food or beverage products flavored with at least one of these enriched compounds, and to a method for the preparation of both diastereoisomers of 3-mercapto-2-methyl-butan-1-ol.

BACKGROUND OF THE INVENTION

In the food and beverage industry flavors play a critical role in the appreciation of food and beverage products. Hereafter the term flavor shall also include aroma and/or taste and in the following context all these terms are used interchangeably.

Several mercapto-alkan-1-ol compounds have been identified as flavorants in food products. Thus, 3-mercapto-hexan-1-ol has been identified in the yellow passion fruit (*Passiflora edulis* f. flavicarpa) (K. -H. Engel, R. Tressel, *J. Agric. Food Chem.* 1991, 39, 2249), in Sauvignon blanc wine (T. Tominaga, A. Furrer, R. Henry, D. Dubourdieu, *Flavour Fragrance J.* 1998, 13, 159; P. Werkhoff, M. G üntert, G. Krammer, H. Sommer, J. Kaulen, *J. Agric. Food Chem.* 1998, 46, 1076), and in red Bordeaux wine (P. Bouchilloux, P. Darriet, R. Henry, V. Lavigne-Cruège, D. Dubourdieu, *J. Agric. Food Chem.* 1998, 46, 3095), and is usually described as having passion fruit and grapefruit character.

3-mercapto-3-methyl-butan-1-ol has been found in roasted coffee (W. Holscher, O. G. Vitzthum, H. Steinhart, *J. Agric. Food Chem.* 1992, 40, 655) and in Sauvignon blanc wine (T. Tominaga, A. Furrer, R. Henry, D. Dubourdieu, *Flavour Fragrance J.* 1998, 13, 159). The flavor description by Holscher et al. is sweet, soup-like.

3-mercapto-2-methyl-propan-1-ol has been identified in red Bordeaux wine (P. Bouchilloux, P. Darriet, R. Henry, V. Lavigne-Cruége, D. Dubourdieu, *J. Agric. Food Chem.* 1998, 46, 3095) and has been described as broth, sweat-like.

The German Offenlegungsschrift 2316456 describes γ-mercapto-alcohols and their formate and acetate esters as important odorants and flavorants that are useful for the preparation and modification of a broad range of flavor compositions. These compounds have been described as faint green, onion-like, sulfury and sweaty with a broad range of taste thresholds.

New 3-mercapto-alkan-1-ols for use as flavor ingredients and/or as flavor enhancers are provided.

SUMMARY OF THE INVENTION

The invention is directed to new 3-mercapto-alkanol compounds. One of these compounds is 3-mercapto-2-methyl-butan-1-ol (formula I)

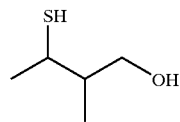

Formula I and stereoisomers of 3-mercapto-2-methyl-butan-1-ol, in which the compound is either enriched for the unlike isomer relative to the like isomer, or is enriched for the like isomer relative to the unlike isomer. The compounds may be enriched for the particular isomer at various ratios.

The invention is also directed to a 3-mercapto-2-methyl-butan-1-ol flavor composition enriched in the unlike isomer relative to the like isomer at ratios of >3:1, >4:1, >6:1, >10:1, >20:1, 30>:1, or >40:1, or enriched in the like isomer relative to the unlike isomer at ratios of >10:1, >20:1, >30:1, >40:1, >50:1, or >100:1. The flavor composition may be enriched in the particular isomer. In one embodiment, the enrichment for unlike isomer relative to the like isomer is in the range of about 6:1 to about 50:1. In another embodiment, the enrichment for unlike isomer relative to the like isomer is in the range from >3:1 to about 50:1. In one embodiment, the enrichment for like isomer relative to the unlike isomer is in the range from about 30:1 to about 100:1. In another embodiment, the enrichment for like isomer relative to the unlike isomer is in the range from >10:1 to about 100:1.

The invention is also directed to a method of flavoring a product by adding to the product 3-mercapto-2-methyl-butan-1-ol (formula I) and stereoisomers of 3-mercapto-2-methyl-butan-1-ol, in which the compound is enriched in the unlike isomer relative to the like isomer, or enriched in the like isomer relative to the unlike isomer, in an amount effective to flavor the product. The product may be a food or beverage, and the compounds may be enriched in the unlike isomer relative to the like isomer at ratios of >3:1, >4:1, >6:1, >10:1, >20:1, >30:1, or >40:1, or in the range of >3:1 to about 50:1, or in the range of about 6:1 to about 50:1, or may be enriched in the like isomer relative to the unlike isomer at ratios of >10:1, >20:1, >30:1, >40:1, >50:1, or >100:1, or in the range of >10:1 to about 100:1, or in the range of about 30:1 to about 100:1.

The invention is also directed to a food or beverage product containing a flavor/aroma composition comprising a 3-mercapto-2-methyl-butan-1-ol enriched in the unlike isomer relative to the like isomer, or enriched in the like isomer relative to the unlike isomer.

Another of these compounds is 3-mercapto-3-methyl-hexan-1-ol (formula II)

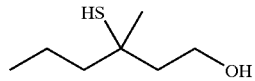

Fomula II and stereoisomers of 3-mercapto-3-methyl-hexan-1-ol.

In one embodiment, the compound is a stereoisomer of 3-mercapto-2-methyl-butan-1-ol having a relative unlike (u) configuration (formula III)

Formula III

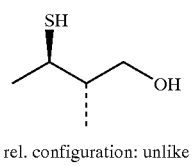

rel. configuration: unlike or the enantiomer of III.

Formula IIIb

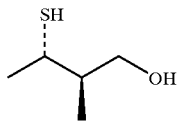

In an alternative embodiment the compound is a diastereomer of 3-mercapto-2-methyl-butan-1-ol having a relative like (l) configuration (formula IV)

Formula IV

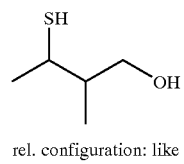

rel. configuration: like or the enantiomer of IV.

The above compounds may be used as flavorants in foods and/or beverages. The 3-mercapto-2-methyl-butan-1-ol and stereoisomer compounds provide cooked vegetable and meaty flavor/aroma notes to food products. The (S) isomer of 3-mercapto-3-methyl-hexan-1-ol enhances meaty notes, while the (R) isomer of 3-mercapto-3-methyl-hexan-1-ol enhances natural fruity character of exotic fruit flavors.

The invention is also directed to a flavor composition containing one or a combination of these compounds. In alternative embodiments, the flavor composition contains (rac)-3-mercapto-3-methyl-hexan-1-ol, (S)-3-mercapto-3-methyl-hexan-1-ol, or (R)-3-mercapto-3-methyl-hexan-1-ol. The compound in the flavor composition is at a concentration in the range of about 0.01 ppb to 50 ppm. The invention is also directed to a food or beverage product containing the above flavor compositions.

The invention is further directed to a method of flavoring a product, such as a food, beverage, oral hygiene product, pharmaceutical, or chewing gum, by adding one or a combination of the above compounds in an amount sufficient to flavor the product. The concentration of the compound may be in the range of about 0.01 ppb to 50 ppm.

The invention is still further directed to methods to synthesize 3-mercapto-2-methyl-butan-1-ol and stereoisomers, and 3-mercapto-3-methyl-hexan-1-ol and stereoisomers.

DETAILED DESCRIPTION

It has now been found that two new mercapto-alkanols, namely 3-mercapto-2-methyl-butan-1-ol of formula I Formula I

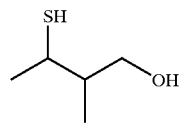

and 3-mercapto-3-methyl-hexan-1-ol of formula II

Fomula II

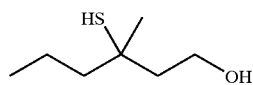

including all possible stereoisomers have very interesting flavor properties that are strongly dependent on the absolute and relative configurations of the compounds.

Especially interesting are the flavor properties of the two diastereoisomeric forms of 3-mercapto-2-methyl-butan-1-ol. As known to one skilled in the art, it will be appreciated that (u)-3-mercapto-2-methyl-butan-1-ol of formula III includes both (S)(R) and (R)(S) enantiomers (formulas IIIa and IIIb, respectively).

Formula IIIa

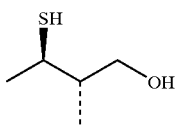

Formula IIIb

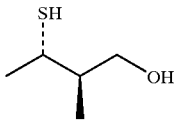

rel. configuration: unlike

As known to one skilled in the art, it will also be appreciated that (l)-3-mercapto-2-methyl-butan-1-ol of formula IV includes both (R)(R) and (S)(S) enantiomers (formulas IVa and IVb, respectively).

Formula IVa

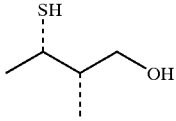

Formula IVb

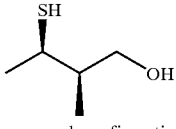

rel. configuration: like which is depicted generally as

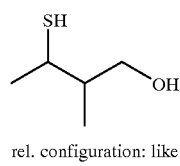

Formula IV rel. configuration: like

It has been found that the (u)-3-mercapto-2-methyl-butan-1-ol enantiomers exhibit a strong onion-like note, with a surprisingly extreme low odor threshold value of 4 pg/l air. Due to this extremely strong aroma, (u)-3-mercapto-2-methyl-butan-1-ol of formula III is a valuable flavor ingredient, and even at concentrations of down to 0.01 ppb in water, the flavor of these compounds can be recognized. It has been found that the enantiomers of formula III are useful to enhance the meaty, boiled meat character of a food product, especially meat products, at concentrations of 0.1 ppb to 1 ppb and to impart cooked vegetable and meaty notes to food products, especially soup products, at concentrations from 1 ppb to 100 ppb.

It has been further found that the (l)-3-mercapto-2-methyl-butan-1-ol enantiomers of formula IV exhibit a herbaceous, onion-like, leeky and gassy character with a far higher threshold value of about 400 pg/l air as compared to the enantiomers of formula III. Surprisingly, it has been found that this compound is useful to enhance the typical natural, fruity character of exotic fruits at concentrations of 10 ppb to 50 ppm in a food product, preferably at concentrations in the range of 100 ppb to 5 ppm. The more enriched for the (l)-3-mercapto-2-methyl-butan-1-ol enantiometers, either (R)(R) or (S)(S), the less of an onion-like note is imparted. Thus, compositions enriched in (l)-3-mercapto-2-methyl-butan-1-ol at a ratio of, e.g., >50:1 or >100:1 relative to (u)-3-mercapto-2-methyl-butanol-1-ol have less of an onion-like note. The same compositions enriched at lower ratios (e.g., >10:1, >20:1 to about 50:1) have more of an onion-like note. These selective enrichments may be used to alter, augment, select, modify, etc., one or more particular flavor/taste/odor properties of the composition and/or the product containing the composition.

Compounds enriched in a particular diastereoisomer, and compositions containing these enriched compounds, are disclosed. The compounds of formulas III and IV are not limited to any particular isomer; all possible enantiomers and all mixtures are thus included within the scope of the invention. The use of these compounds to flavor food and beverage products, and the food and beverage products containing these enriched compounds, are also disclosed. The ratio of the unlike:like configuration in the enriched compositions may be in the range of >3:1, >4:1, >6:1, >10:1, >20:1, >30:1, >40:1 or to about 50:1. In embodiments, enrichment for the unlike configuration may be in the range between >3:1 to about 50:1, or may be in the range between about 6:1 and about 50:1. The ratio of the like:unlike configuration in the enriched compositions may be in the range of >10:1, >20:1, >30:1, >40:1, >50:1, or >100:1. In embodiments, enrichment for the like configuration may be in the range between >10:1 to about 100:1, or may be in the range between about 30:1 and about 100:1. That is, regardless of the total amount of 3-mercapto-2-methyl-butan-1-ol in the composition, the amount of one or the other diastereoisomer will be enriched relative to the other. Such enrichment imparts desirable flavor properties of products, such as food or beverage products.

It has also been found that the two enantiomers of 3-mercapto-3-methyl-hexan-1-ol have quite different olfactory properties, the (S)-isomer exhibits herbaceous, agrestic and green notes whereas the (R)-isomer can be described as grapefruit/passion fruit, black currant and onion-like. Both enantiomers exhibit an extremely strong aroma, even at concentrations of down to 0.1 ppb in water, and are therefore valuable flavor ingredients. The (S)-3-mercapto-3-methyl-hexan-1-ol is useful to enhance the flavor properties of food products, especially the meaty, boiled meat character of meat products the cooked vegetable and meaty notes of soup products. The amount of flavorant needed to impart these flavor characteristics depends on the food product to be flavored and is known to the person skilled in the art. Usually the concentrations range from 0.1 ppb to 1 ppm, preferably from 1 ppb to 100 ppb. The (R)-3-mercapto-3-methyl-hexan-1-ol is useful to enhance the typical natural, fruity character of exotic fruit flavors at concentrations of 10 ppb to 50 ppm in a food product, preferably at concentrations in the range of 100 ppb to 5 ppm.

Depending on the desired flavor properties of the finished food or beverage product, 3-mercapto-3-methyl-hexan-1-ol can be used in enantiomerically pure forms or as mixtures thereof.

The 3-mercapto-alkanols of the present invention are useful for flavoring various products such as foods, beverages, chewing gums, oral hygiene products, and pharmaceuticals, but are especially favored for flavoring foods and beverages. The 3-mercapto-alkan-1-ols according to the present invention can be added directly to the product or as flavor compositions comprising usual additives that are well known to a person of skill in the art. The 3-mercapto-alkan-1-ols according to the present invention can also be used in flavoring compositions to enhance or modify existing flavors in order to provide a specific flavor impression. They may then be incorporated into the flavoring compositions exclusively or in combination with further flavor ingredients such as esters, aldehydes, ketones, alcohols, lactones, heterocycles as e.g. furans, pyridines, pyrazines, and other sulfur compounds as e.g. thiols, sulfides, disulfides and the like. As is known to one of skill in the art, these components can be combined in proportions normally used for flavoring preparation.

It may be desirable to prepare the inventive flavoring compositions by using carrier materials, e.g. gum arabic or maltodextrin, or solvents, e.g. ethanol, propyleneglycol, water or triacetin yielding, inter alia, emulsions. By using carrier materials or solvents, the desired physical form of the flavoring composition can be obtained. When the carrier materials form an emulsion, the flavoring composition may further contain emulsifiers such as mono- and diglycerides of fatty acids and the like. The inventive flavoring compositions may be used in spray-dried, liquid, encapsulated, emulsified, or other forms.

The 3-mercapto-alkan-1-ols of the present invention may be used solely or in combination with other flavor ingredients known by those skilled in the art. Thus, a flavor composition may contain one or more of the compounds according to the invention. The total content of one or more of these compounds is preferably in the range of 0.01 ppb to 50 ppm, preferably in the range of 1 ppb to 5 ppm, depending on the product to be flavored.

The invention also provides a procedure for the stereospecific synthesis of the two diastereoisomeric forms of 3-mercapto-2-methyl-butan-1-ol of formula I, namely (u)-3-mercapto-2-methyl-butan-1-ol of formula III and (l)-3-mercapto-2-methyl-butan-1-ol of formula IV. The procedure for the preparation of (u)-3-mercapto-2-methyl-butan-1-ol comprises the condensation of benzyl mercaptan with angelic acid methyl ester, the reduction of the formed ester with lithium aluminum hydride and subsequent debenzylation with sodium in liquid ammonia. Using this procedure (u)-3-mercapto-2-methyl-butan-1-ol is obtained with a diastereoisomeric purity of >6:1. The isomerically enriched product can be used as such as flavorant to enhance the flavor properties of a food product, or it can be purified by chromatography to get diastereomerically pure (u)-3-mercapto-2-methyl-butan-1-ol, to be rel. configuration: unlike used as flavorant as described infra.

The procedure for the preparation of (l)-3-mercapto-2-methyl-butan-1-ol comprises the condensation of benzyl mercaptan with tiglic acid methyl ester, the reduction of the formed ester with lithium aluminum hydride and subsequent debenzylation with sodium in liquid ammonia. Using this procedure (l)-3-mercapto-2-methyl-butan-1-ol is obtained with a diastereoisomeric purity of >30:1. The isomerically enriched product can be used as such as flavorant to enhance the flavor properties of a food product, or it can be purified by chromatography to get diastereomerically pure (l)-3-mercapto-2-methyl-butan-1-ol, to be rel. configuration: like used as flavorant as described infra.

The present invention is described further in the following examples showing specific embodiments, which are presented solely for the non-limiting purpose of further illustrating the invention.

EXAMPLE 1

Preparation of (rac)-3-mercapto-3-methyl-hexan-1-ol (a) (rac)-3-Methyl-2-hexenoic Acid Ethyl Ester 35.5 g of NaH (0.8 mol, 60% in oil) was washed two times with hexane and suspended in 450 ml of tetrahydrofuran. The suspension was warmed to 35° C. and under stirring 222.2 g (0.98 mole) of triethyl phosphonoacetate was added such that the internal temperature remained between 35–45° C. Then 100 g (1.16 mol) of 2-pentanone was added over a period of thirty min., maintaining a temperature of 40–45° C., and stirring was continued for 1 h. The reaction mixture was cooled to room temperature and the layers were allowed to separate. The lower layer was taken up in 400 ml of $H_2O$ and was extracted three times with 150 ml of hexane. The upper layer and the hexane layers were combined, dried over $Na_2SO_4$ and concentrated in vacuo and gave 172.4 g of a yellowish oil. Distillation at reduced pressure (42 mbar, 92° C.) yielded 119.4 g (77%) of (rac)-3-methyl-2-hexenoic acid ethyl ester.

| | |
|---|---|
| NMR ($CDCl_3$): | 0.93 (t, $CH_3$), 1.27 (t, $CH_3$), 1.50 (m, $CH_2$, isomer B), 1.51 (m, $CH_2$, isomer A), 1.89 (d, $CH_3$, isomer B), 2.10 (d, $CH_2$, isomer A), 2.16, (d, $CH_3$, isomer A), 2.60 (dd, $CH_2$, isomer B), 4.11 (q, $CH_2$, isomer B), 4.12 (q, $CH_2$, isomer A), 5.67 (q, CH) ppm. |
| MS: | 156 (26, $M^+$), 128 (32), 111 (100), 95 (38), 82 (49), 69 (63), 55 (87), 41 (66), 29 (66). |
| IR (neat): | 2962 m, 2936 m, 2874 w, 1718 s, 1649 s, 1218 s, 1149 s, 1106 m, 1040 m. |

(b) (rac)-3-benzylsulfanyl-3-methyl-hexanoic Acid Ethyl Ester

A mixture of 62.1 g (0.5 mol) of benzyl mercaptan and 78.1 g (0.5 mol) of (rac)-3-methyl-2-hexenoic acid ethyl ester of step (a) in 100 ml of piperidine was heated at reflux until complete reaction was observed (48 h), and cooled to room temperature. Then the excess of piperidine was distilled off at reduced pressure (0.04 mbar, 26–33° C.). The residue, 96.5 g (68%) of (rac)-3-benzylsulfanyl-3-methyl-hexanoic acid ethyl ester, was of good purity and was directly used in the next step.

| | |
|---|---|
| NMR ($CDCl_3$): | 0.90 (t, $CH_3$), 1.29 (t, $CH_3$), 1.43 (s, $CH_3$), 1.40–1.65 (m, 2 $CH_2$), 2.61 (s, $CH_2$), 3.75 (s, $CH_2$), 4.16 (q, $CH_2$), 7.15–7.38 (m, 5 arom. H) ppm. |
| MS: | 280 (3, $M^+$), 235 (1), 157 (17), 122 (27), 91 (100), 83 (59), 45 (36), 29 (51). |
| IR (neat): | 2960 m, 2933 m, 2872 w, 1732 s, 1453 m, 1198 m. |

(c) (rac)-3-benzylsulfanyl-3-methyl-hexan-1-ol

At a temperature of 0° C. to a suspension of 6.8 g (0.18 mol) of $LiAlH_4$ in 200 ml of $Et_2O$ was slowly added 50.0 g (0.18 mol) of (rac)-3-benzylsulfanyl-3-methyl-hexanoic acid ethyl ester of step (b) under stirring such that the temperature did not exceed 10° C. Stirring was continued for 1 h and under cooling acetone and then 400 ml of a saturated $NH_4Cl$ solution was slowly added. The reaction mixture was extracted three times with 200 ml of $Et_2O$, the combined organic layers were dried over $Na_2SO_4$ and concentrated in vacuo and gave 40.8 g of a yellowish oil. After drying in high vacuo (0.05 mbar/150° C.) 32.5 g (75%) of (rac)-3-benzylsulfanyl-3-methyl-hexan-1-ol in the form of a yellowish oil was obtained.

| | |
|---|---|
| NMR ($CDCl_3$): | 0.90 (t, $CH_3$), 1.30 (s, $CH_3$), 1.35–1.60 (m, 2 $CH_2$), 1.85 (m, $CH_2$), 2.40 (br., OH), 3.73 (s, $CH_2$), 3.82 (td, $CH_2$), 7.15–7.38 (m, 5 arom. H) ppm. |
| MS: | 238 (4, $M^+$), 114 (13), 97 (40), 91 (89), 55 (100), 41 (28). |
| IR (neat): | 3357 br, 2957 s, 2931 s, 2871 m, 1453 m, 1042 m. |

(d) (rac)-3-mercapto-3-methyl-hexan-1-ol

At a temperature of −78° C. to a solution of 16.0 g (67.1 mmol) of (rac)-3-benzylsulfanyl-3-methyl-hexan-1-ol of step (c) in 200 ml of $Et_2O$ was added from a cylinder about 200 ml of $NH_3$. Then pieces of Na (ca. 4.0 g) were added until the reaction mixture remained blue for more than 20 min. The blue colored mixture was allowed to warm up to room temperature overnight and EtOH was added until the blue color disappeared. The mixture was then acidified with about 2.7 M of HCl, and extracted three times with 150 ml of $Et_2O$. The combined organic layers were dried over $Na_2SO_4$ and concentrated in vacuo. Distillation of the crude product at reduced pressure (40 mbar/130° C.) gave 11.2 g (73%) of (rac)-3-mercapto-3-methyl-hexan-1-ol in form of a colorless oil.

The main flavor was passion fruit, black currant, green.

| | |
|---|---|
| NMR ($CDCl_3$): | 0.94 (t, $CH_3$), 1.37 (s, $CH_3$), 1.38–1.62 (m, 2 $CH_2$), 1.70 (s, SH), 1.88 (m, $CH_2$), 2.30 (br., OH), 3.82 (td, $CH_2$) ppm. |
| MS: | 148 (1, $M^+$), 114 (12), 97 (25), 71 (37), 55 (100), 41 (68). |
| IR (neat): | 3346 br, 2959 s, 2932 s, 2872 m, 1456 m, 1046 m. |

EXAMPLE 2

Preparation of (S)-3-mercapto-3-methyl-hexan-1-ol (a) (rac)-3.5-Dinitro-benzoic Acid 3-mercapto-3-methyl-hexyl Ester To a solution of 5.0 g (34 mmol) of (rac)-3-mercapto-3-methyl-hexan-1-ol in 20 ml of $CCl_4$ was added in portions 8.6 g (37 mmol) of 3,5-dinitrobenzoyl chloride. The mixture was stirred for 72 h, then 10 ml of a saturated NaHCO$_3$ solution was added, the organic layer was separated, washed with 15 ml of brine, dried over MgSO$_4$ and concentrated in vacuo.

The residue was purified by flash-chromatography (silicagel, hexane/EtOAc 4:1) and gave 9.8 g (84%) of (rac)-3,5-dinitro-benzoic acid 3-mercapto-3-methyl-hexyl ester.

| | |
|---|---|
| NMR (CDCl$_3$): | 0.97 (t, CH$_3$), 1.44 (s, CH$_3$), 1.40–1.72 (m, 2 CH$_2$), 1.68 (s, SH), 2.12 (m, CH$_2$), 4.67 (t, CH$_2$), 9.15 (d, 2H), 9.24 (t, 1H) ppm. |
| MS: | 342 (5, M$^+$), 309 (2), 195 (9), 103 (12), 97 (95), 87 (25), 55 (100), 41 (21). |
| IR (neat): | 3101 m, 2961 m, 2933 m, 1732 s, 1629 m, 1547 s, 1463 m, 1345 s, 1279 s, 1168 s. |

(b) (1S,3S)-3,5-Dinitro-benzoic Acid 3-methyl-3-(4,7,7-trimethyl-3-oxo-2-oxa-bicyclo[2.2.1]heptane-1-carbonylsulfanyl)-hexyl Ester To a solution of 9.8 g (28.6 mmol) of (rac)-3,5-dinitro-benzoic acid 3-mercapto-3-methyl-hexyl ester of step (a) and 2.5 g (31.5 mmol) of pyridine in 80 ml of CCl$_4$ was added under stirring 6.82 g (31.5 mmol) of (−)-camphanic acid chloride. The mixture was heated at reflux temperature for 48 h. Another 1.86 g (0.3 eq.) of (−)-camphanic chloride and 0.68 g (0.3 eq.) of pyridine was added and stirring at reflux temperature was continued for 16 h. The mixture was cooled to room temperature, 50 ml of saturated NaHCO$_3$ solution was added and the layers were separated. The organic layer was washed with 40 ml saturated NaHCO$_3$ solution and 40 ml of H$_2$O, dried over MgSO$_4$ and concentrated in vacuo and gave 16.0 g of a yellow oil. Chromatography (silicagel, hexane/EtOAc 4:1) of the crude product yielded 10.0 g of an orange oil. Repeated crystallization from Et$_2$O in the refrigerator gave 1.84 g diastereomerically pure (1S,3S)-3,5-dinitro-benzoic acid 3-methyl-3-(4,7,7-trimethyl-3-oxo-2-oxa-bicyclo[2.2.1]heptane-1-carbonylsulfanyl)-hexyl ester. X-ray study of crystals grown from CH$_3$CN allowed the determination of the absolute configuration at C-3 to be S.

| | |
|---|---|
| NMR (CDCl$_3$): | 0.99 (s, CH$_3$), 1.05 (s, CH$_3$), 1.10, (s, CH$_3$), 1.21 (t, CH$_3$), 1.35–2.05 (m, 7 H), 1.57 (s, CH$_3$), 2.42–2.55 (m, 3H), 4.58 (t, CH$_2$), 9.15 (d, 2H), 9.23 (t, 1H) ppm. |
| MS: | 522 (0.1, M$^+$), 492 (0.5), 309 (15), 214 (3), 195 (3), 55 (62). |
| IR (neat): | 3104 m, 2965 s, 2934 m, 2874 m, 1795 s, 1734 s, 1659 s, 1547 s, 1463 m, 1345 s, 1279 s, 1166 s. |

(c) (S)-3-mercapto-3-methyl-hexan-1-ol

To a suspension of 0.28 g (7.5 mmol) of LiAlH$_4$ in 10 ml of Et$_2$O was added a solution of 1.3 g of (1S,3S)-3,5-dinitro-benzoic acid 3-methyl-3-(4,7,7-trimethyl-3-oxo-2-oxa-bicyclo[2.2.1]heptane-1-carbonylsulfanyl)-hexyl ester of step (b) in 10 ml of THF. The reaction mixture was stirred at room temperature overnight, quenched with 20 ml of water and filtered over Celite. The organic layer was separated, dried over MgSO$_4$ and concentrated in vacuo. The residue was distilled (bulb to bulb, 0.06 Torr, up to 190° C.) and gave 100 mg (27%) of (S)-3-mercapto-3-methyl-hexan-1-ol in form of a colorless oil.

| | |
|---|---|
| NMR (CDCl$_3$): | 0.94 (t, CH$_3$), 1.37 (s, CH$_3$), 1.38–1.62 (m, 2 CH$_2$), 1.70 (s, SH), 1.88 (m, CH$_2$), 2.30 (br., OH), 3.82 (t, CH$_2$) ppm. |
| [α]$_D^{22}$: | −2.5 (c = 0.8, CHCl$_3$) |

The main flavor was herbaceous, agrestic, green.

EXAMPLE 3
Preparation of (l)-3-mercapto-2-methyl-butan-1-ol (Racemic)

(a) (l)-3-benzylsulfanyl-2-methyl-butyric Acid Methyl Ester

At a temperature of 0° C. to a solution of 13.0 ml of n-BuLi (1.6 M in hexane) in 500 ml of THF was added under stirring 236 ml (2.0 mol) of benzyl mercaptan. Then a solution of 23.6 g (0.2 mol) of tiglic acid methyl ester in 500 ml of THF was added. The reaction mixture was allowed to warm up to room temperature and stirring was continued for 3.5 h. The reaction mixture was quenched with 200 ml of a 5% NaOH solution and the organic layer was separated and dried over MgSO$_4$. THF and benzyl mercaptan were distilled off in vacuo (rotary evaporator, 10 mbar/60° C.) and the residue was distilled (0.1 mbar, 110–118° C.) and gave 40.8 g (85.7%) (l)-3-benzylsulfanyl-2-methyl-butyric acid methyl ester in the form of a colorless oil having a diastereoisomeric purity of 98:2 (NMR).

| | |
|---|---|
| NMR (CDCl$_3$): | 1.22 (d, CH$_3$), 1.28 (d, CH$_3$), 2.57 (m, CH), 2.96 (m, CH), 3.64 (s, CH$_3$), 3.72 (s, CH$_2$), 7.15–7.35 (m, 5 arom. H) ppm. |
| MS: | 238 (3, M$^+$), 151 (3), 147 (15), 123 (27), 91 (100), 59 (18). |
| IR (neat): | 3028 w, 2977 m, 2950 m, 1736 s, 1495 m, 1453 s, 1200 m. |

(b) (l)-3-benzylsulfanyl-2-methyl-butan-1-ol

At a temperature of 0° C. to a suspension of 4.78 g (126 mmol) of LiAlH$_4$ in 150 ml of Et$_2$O was added a solution of 20.0 g (84 mmol) of (l)-3-benzylsulfanyl-2-methyl-butyric acid methyl ester of step (a) in 100 ml of Et$_2$O. The reaction mixture was allowed to warm up to room temperature, stirring was continued for 5 h. Then H$_2$O was slowly added until no more H$_2$ evolution was observed. The reaction mixture was filtered over Celite, the organic layer was dried over MgSO$_4$ and concentrated in vacuo. Distillation of the crude product at reduced pressure (0.05 Torr/110° C.) gave 15.5 g (87%) of (l)-3-benzylsulfanyl-2-methyl-butan-1-ol.

| | |
|---|---|
| NMR (CDCl$_3$): | 0.89 (d, CH3), 1.29 (d, CH3), 1.60 (t, OH), 1.87 (m, CH), 2.84 (qd, CH), 3.37–3.68 (m, CH2), 3.74 (d, CH2), 7.18–7.38 (m, 5 arom. H) ppm. |
| MS: | 210 (6, M+), 151 (7), 123 (9), 91 (100), 45 (17), 31 (8). |
| IR (neat): | 3381 br, 3028 w, 2961 s, 2921 s, 2875 s, 1494 m, 1452 s, 1029 s. |

(c) (l)-3-mercapto-2-methyl-butan-1-ol

About 200 ml of NH$_3$ were condensed from a cylinder into a cold flask at −78° C. and small pieces of Na were added until a blue color persisted. Then, under stirring, 3.47 g (64 mmol) of (l)-3-benzylsulfanyl-2-methyl-butan-1-ol were added in small portions. Since the reaction mixture became colorless, the Na addition was continued until a blue color persisted again. Stirring at −78° C. was continued for 1 h, then the mixture was quenched with saturated NH$_4$Cl solution until it became colorless, acidified with 100 ml 2N HCl and extracted with Et$_2$O. The combined organic layers were dried over MgSO$_4$ and concentrated in vacuo. The crude product was distilled at reduced pressure over a 10 cm Vigreux-column (0.15 Torr/60° C.) and gave 5.8 g (86%) (l)-3-mercapto-2-methyl-butan-1-ol in the form of a colorless oil having a diastereoisomeric purity of 40:1 (NMR).

| | |
|---|---|
| NMR (CDCl$_3$): | 0.90 (d, CH$_3$), 1.28 (d, SH), 1.37 (d, CH$_3$), 1.72 (s, OH), 1.86 (m, CH), 3.28 (m, CH), 3.60 (m, CH$_2$) ppm. |
| MS: | 120 (12, M$^+$), 102 (3), 86 (55), 71 (60), 61 (89), 45 (89), 41 (100), 31 (83). |
| IR (neat): | 3356 br, 2964 s, 2926 s, 2876 s, 1450 m, 1379 m, 1039 s. |

The main flavor was herbaceous, onion-like, leeky, gassy.

EXAMPLE 4
Preparation of (u)-3-mercapto-2-methyl-butan-1-ol (Racemic)

(a) (u)-3-benzylsulfanyl-2-methyl-butyric Acid Methyl Ester

At a temperature of 0° C., to a solution of 13.0 ml of n-BuLi (1.6 M in hexane) in 500 ml of THF, was added 236 ml (2.0 mol) of benzyl mercaptan. Then a solution of 23.6 g (0.2 mol) of angelic acid methyl ester in 500 ml of THF was added. The reaction mixture was stirred at 0° C. for 3.5 h, quenched with 200 ml of a 5% NaOH solution. The organic layer was separated and dried over MgSO$_4$. THF and benzyl mercaptan were distilled off in vacuo (rotary evaporator, 10 mbar/60° C.) and the residue was distilled (0.1 mbar, 104–130° C.) and gave 28.2 g (59%) (u)-3-benzylsulfanyl-2-methyl-butyric acid methyl ester in form of a colorless oil having a diastereoisomeric purity of 9:1 (NMR).

| | |
|---|---|
| NMR (CDCl$_3$): | 1.18 (d, CH$_3$), 1.20 (d, CH$_3$), 2.65 (m, CH), 3.03 (m, CH), 3.66 (s, CH$_3$), 3.72 (s, CH$_2$), 7.15–7.35 (m, 5 arom. H) ppm. |
| MS: | 238 (3, M$^+$), 151 (2), 147 (12), 123 (22), 91 (100). |
| IR (neat): | 3029 w, 2975 m, 1736 s, 1495 m, 1453 s, 1199 m. |

(b) (u)-3-benzylsulfanyl-2-methyl-butan-1-ol

At a temperature of 0° C. to a suspension of 4.78 g (126 mmol) of LiAlH$_4$ in 150 ml of Et$_2$O was added under stirring a solution of 20.0 g (84 mmol) of (u)-3-benzylsulfanyl-2-methyl-butyric acid methyl ester in 100 ml of Et$_2$O. The reaction mixture was allowed to warm up to room temperature and stirring was continued for 5 h. Then H$_2$O was slowly added until no more H$_2$ evolution was observed. The reaction mixture was filtered over Celite, the organic layer was dried over MgSO$_4$ and concentrated in vacuo. Distillation of the crude product at reduced pressure (0.05 Torr/100° C.) gave 14.7 g (83%) of (u)-3-benzylsulfanyl-2-methyl-butan-1-ol having a diastereoisomeric purity of 6.5:1 (NMR).

| | |
|---|---|
| NMR (CDCl$_3$): | 0.95 (d, CH$_3$), 1.22 (d, CH$_3$), 1.73 (t, OH), 1.86 (m, CH), 2.78 (m, CH), 3.53 (m, CH$_2$), 3.74 (d, CH$_2$), 7.18–7.38 (m, 5 arom. H) ppm. |
| MS: | 210 (6, M$^+$), 151 (7), 123 (9), 91 (100), 45 (17). |
| IR (neat): | 3377 br, 3028 w, 2963 s, 2923 s, 2875 s, 1494 m, 1452 s, 1029 s. |

(c) (u)-3-benzylsulfanyl-2-methyl-butan-1-ol

About 200 ml of NH$_3$ were condensed into a flask at –78° C. and small pieces of Na were added until a blue color persisted. Then under stirring 9.5 g (40 mmol) of (u)-3-benzylsulfanyl-2-methyl-butan-1-ol of step (b) were added in small portions. Since the reaction mixture became colorless, Na addition was continued until a blue color persisted again. Stirring at –78° C. was continued for 1 h, the mixture was quenched with saturated NH$_4$Cl solution until it became colorless, acidified with 100 ml 2N HCl and extracted with Et$_2$O. The combined organic layers were dried over MgSO$_4$ and concentrated in vacuo. The crude product was distilled at reduced pressure over a 10 cm Vigreux-column (0.06 Torr/47° C.) and gave 3.0 g (62%) (u)-3-mercapto-2-methyl-butan-1-ol in the form of a colorless oil having a diastereoisomeric purity of 6.5:1.

| | |
|---|---|
| NMR (CDCl$_3$): | 1.00 (d, CH$_3$), 1.35 (d, CH$_3$), 1.51 (d, SH), 1.78 (m, CH), 1.97 (br, OH), 3.08 (m, CH), 3.65 (d, CH$_2$). |
| MS: | 120 (13, M$^+$), 102 (4), 86 (58), 71 (62), 61 (90), 45 (79), 41 (100), 31 (76). |
| IR (neat): | 3353 br, 2965 s, 2928 s, 2876 s, 1449 m, 1379 m, 1034 s. |

The main flavor was strong onion-like, brothy character.

EXAMPLE 5
Flavor Tests in Food

A meat base having the following composition (parts by weight), was prepared:

| | |
|---|---|
| water | 10 |
| HVP | 30 |
| thiamin HCl | 10 |
| smoke extract | 50 |
| total | 100 |

With this meat base the following bouillons were prepared:

| Bouillon A (reference) | |
|---|---|
| starting material: bouillon fat free added thereto: | |
| meat base | 100 ppm |

| Bouillon B | |
|---|---|
| starting material: bouillon fat free added thereto: | |
| meat base | 100 ppm |
| (rac)-(u)-3-mercapto-2-methyl-butan-1-ol | 1 ppb |

| Bouillon C | |
|---|---|
| starting material: bouillon fat free added thereto: | |
| meat base | 100 ppm |
| (R)-3-mercapto-3-methyl-hexan-1-ol | 1 ppb |

Bouillons A and B were compared in a blind test by an expert panel of six flavorists. The panel judged bouillon B to have a fuller, more bouillon-like aroma with increased meaty and fatty notes.

Bouillons A and C were compared in a blind test by an expert panel of six flavorists. The panel judged bouillon C to have a fuller, sweeter, more bouillon-like aroma with increased chicken-meat, fatty and onion notes.

Thus, in both tests the present flavor components enhanced the bouillon or meat character, respectively.

EXAMPLE 6

Flavor Test in Beverage

Flavoring compositions A and B having a passion fruit flavor were prepared using the following ingredients (parts by weight):

| Ingredient | A | B |
|---|---|---|
| Hexyl butyrate | 96 | 96 |
| Ethyl hexanoate | 82 | 82 |
| cis-3-Hexenol | 86 | 86 |
| Linalool | 31 | 31 |
| Hexanal | 9 | 9 |
| Citral | 11 | 11 |
| Methyl 2-octenoate | 34 | 34 |
| Furonol | 48 | 48 |
| Hexanoic acid | 68 | 68 |
| Orange oil | 247 | 207 |
| Ocimene | 69 | 69 |
| 2-Methyl-heptanoic acid | 27 | 27 |
| 2-Hexenoic acid | 137 | 137 |
| cis-3-Hexenyl acetate | 55 | 55 |
| (rac)-3-Mercapto-3-methyl-hexan-1-ol | — | 40 |
| Total | 1000 | 1000 |

The passion fruit flavoring compositions A and B were added, at two drops per 100 ml beverage (about 200 mg/l), to a standard still beverage that was prepared by 1+5 dilution of a beverage syrup of the following composition (parts by weight):

| Ingredient | |
|---|---|
| Sugar Syrup, 65 Bx | 1033 |
| Sodium benzoate | 1 |
| Trisodium citrate | 2 |
| Citric acid anhydrous, 50%$^{w/w}$ in water | 30 |
| Water, cold, filled up to 1000 ml | |

The thus prepared passion fruit drink AA containing the flavoring composition A, and the passion fruit drink BB containing the flavoring composition B with about 5 ppm of a compound of the present invention, namely (rac)-3-mercapto-3-methyl-hexan-1-ol, were evaluated in a blind test by an expert panel of six flavorists. The panel judged the passion fruit drink BB to have a more rounded off passion fruit flavor with typical exotic fruit character, having a greener, fresher and fruitier character than fruit drink AA.

While the invention has been illustrated and described with respect to illustrative embodiments and modes of practice, it will be apparent to those skilled in the art that various modifications and improvements may be made without departing from the scope and spirit of the invention. Accordingly, the invention is not be limited to the illustrative embodiments and modes or practice.

What is claimed is:

1. A 3-mercapto-2-methyl-butan-1-ol enriched in the diastereomer having the formula (u)-3-mercapto-2-methyl-butan-1-ol and enantiomers thereof

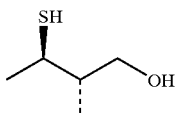

Formula IIIa

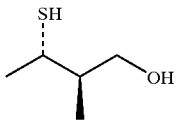

Formula IIIb rel. configuration: unlike relative to (l)-3-mercapto-2-methyl-butan-1-ol (formula IV) and enantiomers thereof

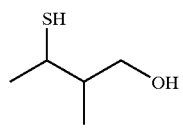

IV rel. configuration: like.

2. The 3-mercapto-2-methyl-butan-1-ol of claim 1 wherein the unlike enantiomer is selected from the group consisting of (R)(S)-3-mercapto-2-methyl-butan-1-ol and (S)(R)-3-mercapto-2-methyl-butan-1-ol and is enriched over like enantiomers (R)(R)-3-mercapto-2-methyl-butan-1-ol and (S)(S)-3-mercapto-2-methyl-butan-1-ol.

3. The 3-mercapto-2-methyl-butan-1-ol of claim 1 enriched in (S)(R)-3-mercapto-2-methyl-butan-1-ol.

4. The 3-mercapto-2-methyl-butan-1-ol of claim 1 enriched in (R)(S)-3-mercapto-2-methyl-butan-1-ol.

5. The 3-mercapto-2-methyl-butan-1-ol of claim 1 wherein (u)-3-mercapto-2-methyl-butan-1-ol is enriched at a ratio chosen from at least one of >3:1, >4:1, >6:1, >10:1, >20:1, >30:1, and >40:1 relative to (l)-3-mercapto-2-methyl-butan-1-ol.

6. The 3-mercapto-2-methyl-butan-1-ol of claim 1 enriched for the unlike form at a ratio >3:1 to about 50:1 relative to the like form.

7. The 3-mercapto-2-methyl-butan-1-ol of claim 1 enriched for the unlike form at a ratio from about 6:1 to about 50:1 relative to the like form.

8. A 3-mercapto-2-methyl-butan-1-ol enriched in the diastereomer having the formula (l)-3-mercapto-2-methyl-butan-1-ol (formula IV) and enantiomers thereof

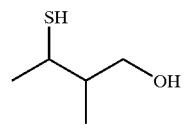

IV rel. configuration: like relative to (u)-3-mercapto-2-methyl-butan-1-ol and enantiomers thereof

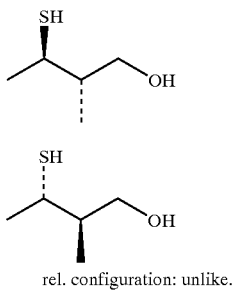

Formula IIIa

Formula IIIb rel. configuration: unlike.

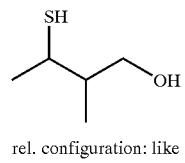

rel. configuration: like

9. The 3-mercapto-2-methyl-butan-1-ol of claim 8 wherein the like enantiomer is selected from the group consisting of (R)(R)-3-mercapto-2-methyl-butan-1-ol and (S)(S)-3-mercapto-2-methyl-butan-1-ol and is enriched over unlike enantiomers (R)(S)-3-mercapto-2-methyl-butan-1-ol and (S)(R)-3-mercapto-2-methyl-butan-1-ol.

10. The 3-mercapto-2-methyl-butan-1-ol of claim 8 enriched in (R)(R)-3-mercapto-2-methyl-butan-1-ol.

11. The 3-mercapto-2-methyl-butan-1-ol of claim 8 enriched in (S)(S)-3-mercapto-2-methyl-butan-1-ol.

12. The 3-mercapto-2-methyl-butan-1-ol of claim 8 wherein (l)-3-mercapto-2-methyl-butan-1-ol is enriched at a ratio chosen from at least one of >10:1, >20:1, >30:1, >40:1, >50:1 to about 100:1 relative to (l)-3-mercapto-2-methyl-butan-1-ol.

13. The 3-mercapto-2-methyl-butan-1-ol of claim 8 enriched for the like form at a ratio >10:1 to about 100:1 relative to the unlike form.

14. The 3-mercapto-2-methyl-butan-1-ol of claim 8 enriched for the like form at a ratio from about 30:1 to about 100:1 relative to the unlike form.

15. A flavor composition comprising (a) a (u)-3-mercapto-2-methyl-butan-1-ol diastereoisomer of 3-mercapto-2-methyl-butan-1-ol and enantiomers thereof,

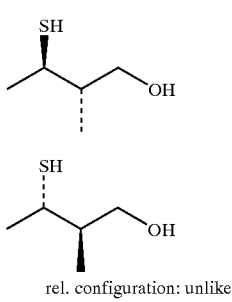

Formula IIIa

Formula IIIb rel. configuration: unlike and (b) a (l)-3-mercapto-2-methyl-butan-1-ol (formula IV) diastereoisomer of 3-mercapto-2-methyl-butan-1-ol and enantiomers thereof, the composition enriched in the diastereoisomer and enantiomers in (a) in relation to (b), or the diastereoisomer and enantiomers in (b) in relation to (a).

16. The composition of claim 15 wherein the unlike entaniomer is selected from the group consisting of (R)(S)-3-mercapto-2-methyl-butan-1-ol and (S)(R)-3-mercapto-2-methyl-butan-1-ol and is enriched over like enantiomers (R)(R)-3-mercapto-2-methyl-butan-1-ol and (S)(S)-3-mercapto-2-methyl-butan-1-ol.

17. The composition of claim 15 wherein the like entaniomer is selected from the group consisting of (R)(R)-3-mercapto-2-methyl-butan-1-ol and (S)(S)-3-mercapto-2-methyl-butan-1-ol and is enriched over unlike enantiomers (R)(S)-3-mercapto-2-methyl-butan-1-ol and (S)(R)-3-mercapto-2-methyl-butan-1-ol.

18. The composition of claim 15 enriched in (S)(R)-3-mercapto-2-methyl-butan-1-ol.

19. The composition of claim 15 enriched in (R)(S)-3-mercapto-2-methyl-butan-1-ol.

20. The composition of claim 15 enriched in (R)(R)-3-mercapto-2-methyl-butan-1-ol.

21. The composition of claim 15 enriched in (S)(S)-3-mercapto-2-methyl-butan-1-ol.

22. The composition of claim 15 wherein (u)-3-mercapto-2-methyl-butan-1-ol (formula III) is enriched at a ratio chosen from at least one of >3:1, >4:1, >6:1, >10:1, >20:1, >30:1, >40:1, between >3:1 to about 50:1, and from about 6:1 to about 50:1 relative to (l)-3-mercapto-2-methyl-butan-1-ol.

23. The composition of claim 15 wherein (l)-3-mercapto-2-methyl-butan-1-ol (formula IV) is enriched at a ratio chosen from at least one of >10:1, >20:1, >30:1, >40:1, >50:1, >100:1, between >10:1 to about 100:1, and from about 30:1 to about 100:1 relative to (u)-3-mercapto-2-methyl-butan-1-ol.

24. The composition of claim 15 wherein a concentration of said diastereoisomers is the range of about 0.01 ppb to about 50 ppm.

25. The composition of claim 15 wherein a concentration of said diastereoisomers is in the range of about 1 ppb to about 5 ppm.

26. A method of flavoring a product comprising adding to said product a flavor composition comprising
(a) a (u)-3-mercapto-2-methyl-butan-1-ol (formula III) diastereoisomer of 3-mercapto-2-methyl-butan-1-ol and enantiomers thereof, Formula IIIa

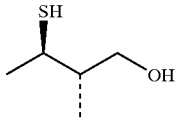

-continued

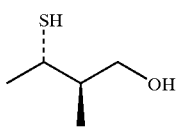

Formula IIIb rel. configuration: unlike and,
(b) a (l)-3-mercapto-2-methyl-butan-1-ol (formula IV) a diastereoisomer of 3-mercapto-2-methyl-butan-1-ol and enantiomers thereof,

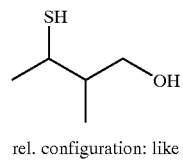

IV rel. configuration: like the composition enriched in the diastereoisomer and enantiomers in (a) in relation to (b), or the diastereoisomer and enantiomers is (b) in relation to (a), in an amount effective to flavor the product.

27. The method of claim 26 adding the composition enriched in unlike (R)(S)-3-mercapto-2-methyl-butan-1-ol.

28. The method of claim 26 adding the composition enriched in unlike (S)(R)-3-mercapto-2-methyl-butan-1-ol.

29. The method of claim 26 adding the composition enriched in like (S)(S)-3-mercapto-2-methyl-butan-1-ol.

30. The method of claim 26 adding the composition enriched in like (R)(R)-3-mercapto-2-methyl-butan-1-ol.

31. The method of claim 26 wherein (u)-3-mercapto-2-methyl-butan-1-ol (formula III) is enriched at a ratio chosen from at least one of >3:1, >4:1, >6:1, >10:1, >20:1, >30:1, >40:1, between >3:1 to about 50:1, and from about 6:1 to about 50:1 relative to (l)-3-mercapto-2-methyl-butan-1-ol.

32. The method of claim 26 wherein (l)-3-mercapto-2-methyl-butan-1-ol (formula IV) is enriched at a ratio chosen from at least one of >10:1, >20:1, >30:1, >40:1, >50:1, >100:1, between >10:1 to about 100:1, and from about 30:1 to about 100:1 relative to (u)-3-mercapto-2-methyl-butan-1-ol.

33. The method of claim 26 wherein the product is a food or beverage product.

34. The method of claim 26 wherein said amount produces a concentration in the range of about 0.01 ppb to about 50 ppm.

35. The method of claim 26 wherein said amount is in the range of about 1 ppb to about 5 ppm.

36. The method of claim 26 wherein said product is selected from a food product, a beverage product, an oral hygiene product, a pharmaceutical, chewing gum, and combinations thereof.

37. The method of claim 26 wherein said product is selected from the group consisting of a meat product, a vegetable product, and combinations thereof.

38. The method of claim 26 wherein said flavoring is selected from the group consisting of onion-like brothy, herbaceous onion-like leeky gassy, herbaceous agrestic green, grapefruit/passion fruit black currant green, and combinations thereof.

39. The method of claim 26 wherein said composition is added to said food or beverage product in a form consisting of spray dried, liquid, encapsulated, emulsified, and combinations thereof.

40. A flavorant composition comprising (u)-3-mercapto-2-butan-1-ol

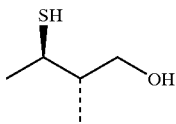

Formula IIIa

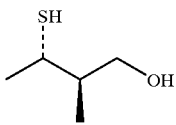

Formula IIIb rel. configuration: unlike enriched relative to (l)-3-mercapto-2-butan-1-ol (formula IV)

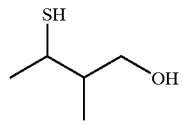

Formula IV rel. configuration: like having a meaty cooked vegetable taste and an odor threshold of 4 pg/l air.

41. A method of flavoring a food or beverage product comprising providing a composition selectively enriched at a ratio of at least greater than 3:1 in (u)-3-mercapto-2-butan-1-ol (formula III)

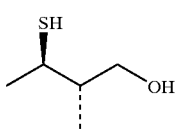

Formula IIIa

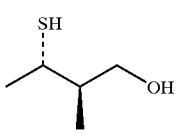

Formula IIIb rel. configuration: unlike relative to (l)-3-mercapto-2-butan-1-ol (formula IV)

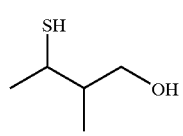

Formula IV rel. configuration: like to the food or beverage product at a concentration in the range of about 0.1 ppb to about 100 ppb.

42. A flavorant composition comprising (l)-3-mercapto-2-butan-1-ol (formula IV)

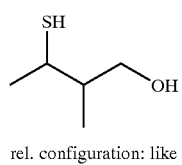

rel. configuration: like enriched relative to (u)-3-mercapto-2-butan-1-ol

Formula IIIa

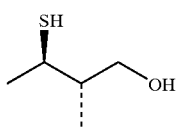

Formula IIIb rel. configuration: unlike having a herbaceous onion-like leeky gassy taste and an odor threshold of 400 pg/l air.

43. A method of flavoring a food or beverage product comprising providing a composition selectively enriched at a ratio of at least greater than 10:1 in (l)-3-mercapto-2-butan-1-ol (formula IV)

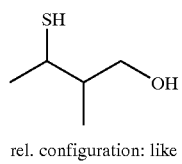

rel. configuration: like relative to (u)-3-mercapto-2-butan-1-ol

Formula IIIa

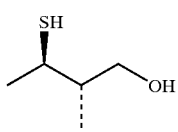

Formula IIIb

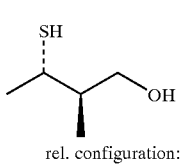

rel. configuration: unlike to the food or beverage product at a concentration in the range of about 10 ppb to about 5 ppm.

44. A food or beverage product containing a flavor/aroma composition comprising a 3-mercapto-2-methyl-butan-1-ol enriched by a ratio of at least greater than 3:1 for the diastereomer having the formula (u)-3-mercapto-2-methyl-butan-1-ol (formula III) and enantiomers thereof Formula IIIa

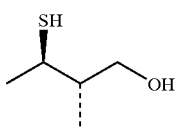

Formula IIIb

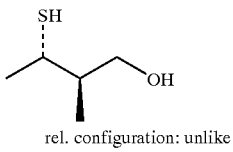

rel. configuration: unlike relative to (l)-3-mercapto-2-methyl-butan-1-ol (formula IV)

Formula IV

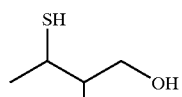

rel. configuration: like and enantiomers thereof.

45. The food or beverage product of claim 44 enriched to about 50:1.

46. A food or beverage product containing a flavor/aroma composition comprising a 3-mercapto-2-methyl-butan-1-ol enriched by a ratio of at least greater than 10:1 for the diastereomer having the formula (l)-3-mercapto-2-methyl-butan-1-ol (formula IV) and enantiomers thereof

IV

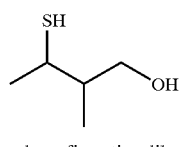

rel. configuration: like relative to (u)-3-mercapto-2-methyl-butan-1-ol (formula III)

Formula IIIa

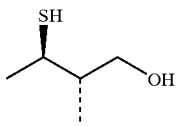

Formula IIIb

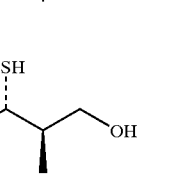

rel. configuration: unlike and enantiomers thereof.

47. The food or beverage product of claim 46 enriched to about 100:1.

* * * * *

UNITED STATES PATENT AND TRADEMARK OFFICE
CERTIFICATE OF CORRECTION

PATENT NO. : 6,805,893 B2
DATED : October 19, 2004
INVENTOR(S) : Acuña et al.

It is certified that error appears in the above-identified patent and that said Letters Patent is hereby corrected as shown below:

Title page,
Item [75], Inventors, "Gonzalo Acuna" should be -- Gonzalo Acuña --
Item [56], References Cited, FOREIGN PATENT DOCUMENTS, "GB 1429314" should be -- GB 1423914 --
OTHER PUBLICATIONS, "Engel et al.," reference, "...Yelloow Passion Fruits..." should be -- Yellow Passion Fruits --
"Olsen et al.," reference, "(1968)" should read -- (1988) --
"Werkhoff et al.," reference, "...Yelow Passion Fruits..." should be -- Yellow Passion Fruits --

Column 2,
Line 19, "...30>:1, or..." should be -- ...>30:1, or... --

Column 6,
Line 11, "...boiled meat character of meat products the cooked vegetable..." should be -- boiled meat character of meat products and the cooked vegetable --
Line 63, "...(rac)-3.5-Dinitrobenzoic Acid..." should be -- ...(rac)-3,5-Dinitro-benzoic Acid... --

Column 9,
Line 22, "...Ester" should be -- ester --

Column 10,
Line 49, "...0.89 (d, CH3), 1.29 (d, CH3),..." should be -- ...0.89 (d, $CH_3$), 1.29 (d, $CH_3$),... --
Line 54, "...(m, CH2), 3.74 (d, CH2), ..." should be -- ...(m, $CH_2$), 3.74 (d, $CH_2$),... --
Line 55, "...(6, M+),..." should be -- ...(6, $M^+$),... --

Column 13,
Line 61, "...the invention is not be limited to the..." should be -- the invention is not to be limited to the... --

Column 16,
Line 50, "...a concentration of said diastereoisomers is the range of about..." should be -- a concentration of said diastereoisomers is in the range of about... --

Column 17,
Line 25, "or the diastereoisomer and enantiomers is (b) in relation to (a),..." should be -- or the diasteroisomer and enantiomers in (b) in relation to (a),... --

UNITED STATES PATENT AND TRADEMARK OFFICE
CERTIFICATE OF CORRECTION

PATENT NO. : 6,805,893 B2
DATED : October 19, 2004
INVENTOR(S) : Acuña et al.

It is certified that error appears in the above-identified patent and that said Letters Patent is hereby corrected as shown below:

Column 18,
Lines 1 and 37, "…(u)-3-mercapto-2-butan-1-ol…" should be -- …(u)-3-mercapto-2-methyl-butan-1-ol… --
Line 19, "…(l)-3-mercapto-2-butan-1-ol…" should be -- …(l)-3-mercapto-2-methyl-butan-1-ol… --
Line 55, "…(l)-3-mercapto-2-butan-1-ol…" should be -- …(u)-3-mercapto-2-methyl-butan-1-ol… --

Column 19,
Lines 1-2 and 33, "…(l)-3-mercapto-2-butan-1-ol…" should be -- …(l)-3-mercapto-2-methyl-butan-1-ol… --
Lines 12 and 45, "…(u)-3-mercapto-2-butan-1-ol…" should be -- …(u)-3-mercapto-2-methyl-butan-1-ol… --
Line 62, "…about 10 ppb to about 5 ppm." should be -- about 10 ppb to about 50 ppm. --

Signed and Sealed this

Thirty-first Day of May, 2005

JON W. DUDAS
*Director of the United States Patent and Trademark Office*